United States Patent [19]
Cosgrove, Jr. et al.

[11] Patent Number: 4,578,244
[45] Date of Patent: Mar. 25, 1986

[54] SAMPLING APPARATUS FOR OBTAINING A PLURALITY OF FLUID SAMPLES

[75] Inventors: Robert J. Cosgrove, Jr., Wanaque, N.J.; Victor F. Smolen, West Palm Beach, Fla.

[73] Assignee: Pharmacontrol Corp., Englewood Cliffs, N.J.

[21] Appl. No.: 371,248

[22] Filed: Apr. 23, 1982

[51] Int. Cl.$^4$ ............................................. G01N 35/02
[52] U.S. Cl. ..................... 422/65; 73/432 R; 73/432 SD; 366/331; 366/605; 422/67; 422/81; 422/102; 436/34
[58] Field of Search ............ 73/432 R, 432 SD; 366/314, 331, 605; 422/63, 64, 65, 67, 68, 81, 102; 436/34

[56] References Cited
U.S. PATENT DOCUMENTS

| Re. 30,627 | 5/1981 | Bagshawe et al. | 422/63 X |
| 3,223,486 | 12/1965 | Holl, Jr. et al. | 366/314 X |
| 3,606,260 | 9/1971 | Rubin | 366/331 X |
| 3,787,185 | 1/1974 | Rohrbaugh et al. | 366/331 X |
| 4,108,602 | 8/1978 | Hanson et al. | 422/67 X |
| 4,158,694 | 6/1979 | Bischoff et al. | 422/103 X |
| 4,279,860 | 7/1981 | Smolen | 422/100 X |

FOREIGN PATENT DOCUMENTS 466017  6/1975  U.S.S.R. ............................. 422/65

Primary Examiner—Arnold Turk
Attorney, Agent, or Firm—Pennie & Edmonds

[57] ABSTRACT

A sampling apparatus for obtaining a plurality of fluid samples is disclosed, such sampling apparatus being particularly useful in connection with dissolution testing of various products. The apparatus includes a plurality of sampling containers each having a chamber therein for receipt of a fluid, and a drive device for simultaneously moving the plurality of sample containers to a sampling station. First fluid conduits are provided for each of the sampling containers for conducting a fluid into each of the sampling containers when the sampling containers are positioned at the sampling station, and second fluid conduits are provided for each of the sampling containers for withdrawing a sample fluid from each of the sampling containers when the sampling containers are positioned at the sampling station. Devices are provided for coupling the first and second fluid conduits with the chambers of each of the sampling containers when the sampling containers are positioned at the sampling station, such devices in addition being adapted to individually seal the chambers of each of the sampling chambers when the first and second fluid conduits are coupled thereto. In the preferred embodiment, each of the sampling containers also includes an agitation element for agitating fluid introduced into the containers at the sampling station.

25 Claims, 10 Drawing Figures

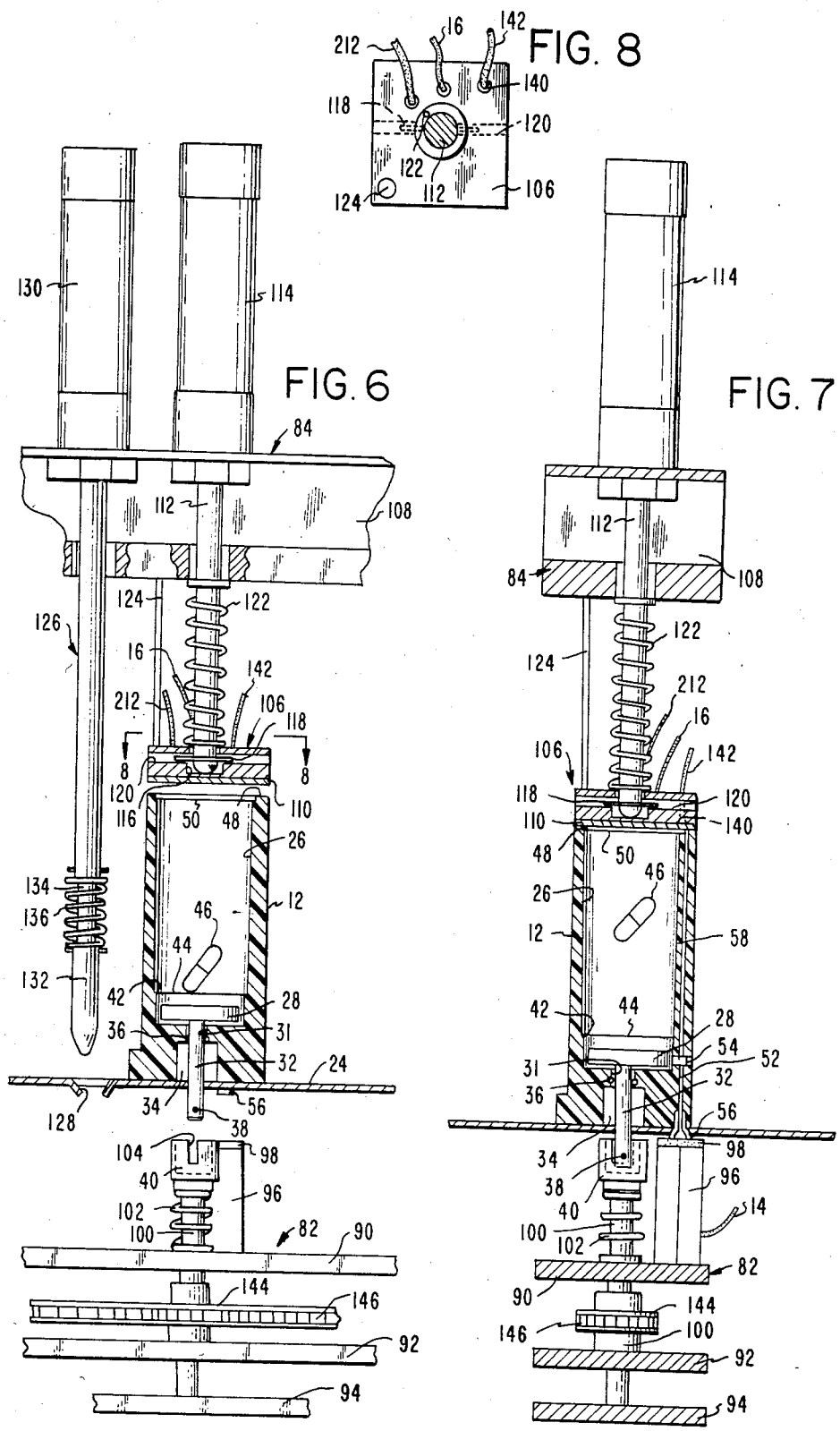

SAMPLING APPARATUS FOR OBTAINING A PLURALITY OF FLUID SAMPLES

FIELD OF THE INVENTION

The present invention relates generally to a sampling apparatus for obtaining fluid samples, and more particularly to a sampling apparatus for obtaining a plurality of fluid samples in a more efficient and less time consuming manner.

The sampling apparatus of the present invention is particularly useful in connection with automatic dissolution testing of products whose solubility and dissolution rate properties affect product performance. In this regard, the term dissolution will be used herein in a broad sense to refer to the act of substances going into solution or forming colloidal suspensions, and not necessarily to the particular process by which such act occurs. Such processes, for example, may comprise the dissolving of substances, chemical erosion, diffusion, the formation of colloidal suspensions and the like. It should be appreciated, however, that the sampling apparatus of the present invention is not limited to use in connection with dissolution testing, but rather has applicability to other types of testing and analyses in which it is desired to obtain more quickly and efficiently a plurality of samples of a generally uniform nature.

BACKGROUND OF THE INVENTION

Dissolution testing of components of industrial products whose solubility and dissolution rate properties affect product performance can be used as a screening and quality control tool. Solubility properties of solid materials can depend on polymorphic crystalline form, crystal habit, crystal shape, particle size and particle size distribution, and state of solvation. A simple and rapidly performed dissolution test can substitute for the determination of these physical properties by more time consuming and differential thermal analysis, microscopy, etc. The properties instead may be determined with reference to whether they conform to a dissolution rate standard under specified conditions and in relation to a known reference sample of the same material characterized by the above physical properties and possessing the derived dissolution rate and solubility performance.

As noted in U.S. Pat. No. 4,279,860, entitled "Multiple Injector Flow Through Dissolution Cell For Dissolution Testing Apparatus," the broad technique of determining dissolution rate properties is especially of interest in the testing of drug products where the therapeutic performance of drugs is closely related to the drug dissolution properties. Such techniques, for example, can be used as a quality control tool, such as in an in vivo bioequivalency requirement for multisource generic drug products, or as a substitute for human bioavailability testing during the development of new drug product formulations. The principles behind such interest are more fully discussed in the aforementioned U.S. Pat. No. 4,279,860 as well as in U.S. Pat. No. 4,335,438. As noted in such patent and patent application, it is important that the dissolution tests in connection with such uses provide predictive results that are biologically relevant.

While the aforementioned U.S. Pat. No. 4,279,860 discloses and describes a multiple injector flow through dissolution cell for use in such a dissolution testing apparatus which is particularly useful in connection with testing of rapidly dissolving industrial products or drug dosage forms, the dissolution cell disclosed therein is only operative to produce a single sample solution at any given instant, thereby limiting its effectiveness in connection with producing a large number of samples and conducting necessary tests thereon.

As can be appreciated, it is desirable to provide the capability of increasing the rate at which fluid samples may be produced, while at the same time providing for uniformity and repeatability of producing test samples to provide accurate and correct dissolution rate and solubility performance information. Further, it is desirable to provide an apparatus which is not subject to problems associated with cleaning out test cells after samples have been taken, or problems associated with leakage of fluids introduced into the various cells. The present invention achieves these desirable principles in connection with a sampling apparatus so as to provide the capability of providing for a more efficient, quick, uniform and repeatable production of fluid samples, and which is particularly useful in a dissolution testing system.

SUMMARY OF THE INVENTION

In accordance with one aspect of the present invention, there is provided a sampling apparatus for obtaining a plurality of fluid samples. The apparatus comprises a plurality of sampling containers each of which has a chamber therein for receipt of a fluid. Drive means are provided for simultaneously moving the plurality of sampling containers to a sampling station of the apparatus. First fluid conducting means are also included for each of the sampling containers for conducting a fluid into each of the sampling containers when the sampling containers are positioned at the sampling station, and second fluid conducting means are provided for each of the sampling containers for withdrawing a fluid sample therefrom when the sampling containers are positioned at the sampling station. In addition, coupling means are provided for coupling the first and second fluid conducting means with the chambers of each of the sampling containers when the sampling containers are positioned at the sampling stations. The coupling means includes sealing means for individually sealing the chamber of each of the sampling containers when the first and second fluid conducting means are coupled thereto.

Thus, with such an apparatus a plurality of sampling containers are moved simultaneously to a sampling station where first and second fluid conducting means are coupled to each of the chambers of the sampling containers for the introduction into and withdrawal of fluid from the sampling containers. When the first and second fluid conducting means are coupled to the chambers, each of the chambers is individually sealed by sealing means associated with the coupling means. In this way, substantially closed chambers will be provided for the introduction of fluid into the chamber and withdrawal of the sample fluid therefrom, thereby insuring the integrity of the overall apparatus to produce desired fluid samples.

In one embodiment of the present invention, the chambers of the sampling containers each include a substance to be dissolved in the fluid introduced thereinto, and, after the substance has been dissolved or during the dissolution process, a fluid sample is withdrawn and conducted to a suitable test apparatus for measuring the concentration of the substance contained in the sample fluid. Thus, with the present invention in which a plurality of sampling containers are provided at the sampling station, the number of samples which may be taken at any given time can be greatly increased.

In accordance with the preferred embodiment of the sampling apparatus, the sampling apparatus includes various features and structures for enhancing the alignment of the sampling containers with the input and output fluid conducting means, thereby insuring substantially automatic positioning of the sampling containers for sampling operations to produce a plurality of fluid samples. For instance, in the preferred embodiment, the sealing of the sampling containers having the fluid conduits coupled thereto is accomplished by a clamping arrangement in which each of the sampling containers is individually clamped between upper and lower seal assemblies, the fluid conducting means in turn being mounted on the upper and lower seal assemblies and communicating with the chambers through inlet and outlet ports in the containers. Because of this clamping type seal arrangement, the containers may be moved into and out of position for sampling operations by simply moving the upper and lower seal assemblies apart from one another and allowing the containers to move freely laterally therebetween. Once they are in position, the clamping action is applied to seal the chambers and in particular the openings into and out of the chamber through which the first and second fluid conducting means communicate.

Also in the preferred embodiment, the sampling containers are all mounted on a tray member which is laterally movable into position between the upper and lower seal assemblies, and then lowered onto the lower seal assemblies when the sampling containers are at the sampling station, the upper seal assembly then being actuated to lower the upper seal members into engagement with the upper ends of the containers and to clamp the containers between upper and lower sealing members. To facilitate alignment of the sampling containers with the fluid conducting means, the apparatus includes guide pins which are adapted to move toward the tray and into engagement with guide openings therein to laterally position the tray to aid in precise alignment of the individual sampling containers.

In accordance with another aspect of the present invention, each of the sampling containers includes individual agitation means associated therewith and which is operable for agitating material in the chamber. Operating means are provided for operating each of the individual agitation means when the sampling containers are positioned at the sampling stations. Such agitation means will serve to improve the mixing efficiency of the substances contained within the sampling containers. In the preferred embodiment, the agitation means comprises a rotatable agitation member mounted within the chamber of each sampling container and having a drive shaft extending outwardly from the bottom end thereof. When the sampling containers are lowered onto the lower seal assembly, the drive shaft is engagable by a rotatable coupling device for rotating the agitating members. To insure receipt of the drive shaft within the drive coupling device, the opening in the rotatable coupling device is of a slightly larger lateral dimension than the lateral dimension of the drive shaft of the agitating means.

Still further in accordance with the preferred embodiment, the sampling containers are each constructed so as to be able to receive an insert member which serves to longitudinally divide the chamber into first and second subchambers. The insert member has a longitudinally extending wall for this purpose which includes a passageway therethrough, and means for mounting a material thereto. Such an insert member is most useful in connection with conducting permeability testing with respect to certain materials and substances.

These and further features and characteristics of the present invention will be apparent from the following detailed description in which reference is made to the enclosed drawings which illustrate preferred embodiments of the present invention.

BRIEF DESCRIPTION OF THE DRAWINGS

FIG. 6 is an enlarged elevational view, partly in section, taken along lines 6—6 of FIG. 2 and illustrating the relationship between a single sampling container and the upper and lower seal assemblies before coupling of fluid conduits to the sampling containers.

FIG. 7 is an enlarged elevational view, partly in section, taken along lines 7—7 of FIG. 2 and illustrating the relationship between a single sampling container and the upper and lower seal assemblies after coupling of fluid conduits to the sampling container, the view of FIG. 7 being substantially at 90° relative to the view of FIG. 6.

FIG. 8 is a sectional view taken along lines 8—8 of FIG. 6.

DETAILED DESCRIPTION OF THE PREFERRED EMBODIMENTS

Figure 1:
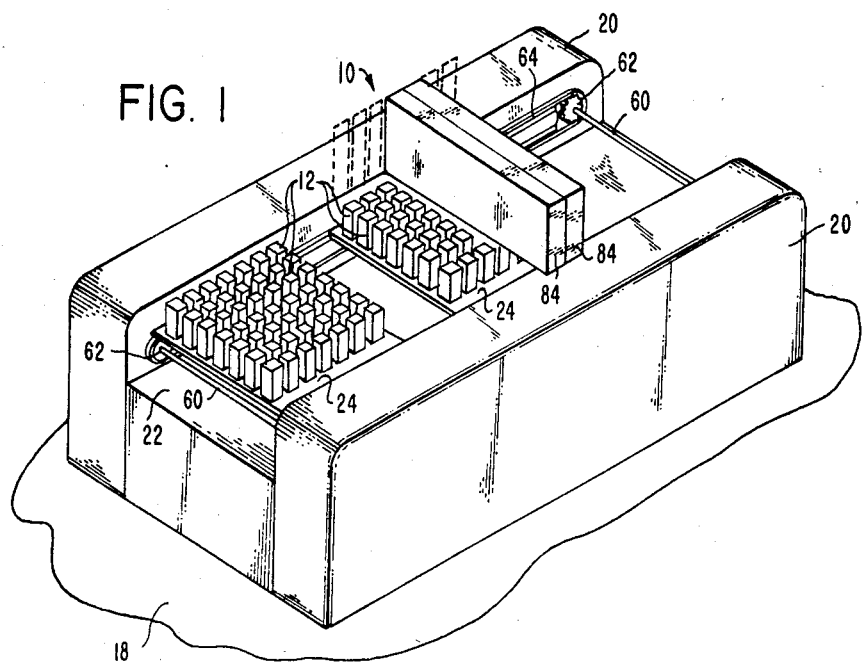
FIG. 1 is a perspective view of the sampling apparatus in accordance with the present invention, and illustrating the apparatus being used in connection with the obtaining of fluid samples from a plurality of sampling containers.

Referring now to the drawings wherein like reference characters represent like elements, there is shown in FIG. 1 a sampling apparatus 10 in accordance with the present invention. As such sampling apparatus 10 is particularly useful in connection with the obtaining of fluid samples for use in a dissolution testing system, the description and operation of such apparatus 10 will be made with reference to such a system. However, it should be appreciated that the apparatus 10 could also be used in connection other systems for obtaining fluid samples, and therefore the description of the sampling apparatus 10 in connection with a dissolutioned testing system should not be taken as being limiting of the scope of the present invention.

The sampling apparatus 10 is generally operable to receive a plurality of sampling containers 12 and to transport them to a sampling station where fluid conduits 14, 16 are coupled to the sampling containers 12 for introducing fluid into the sampling containers 12 and for withdrawing a fluid sample therefrom. More particularly, at the sampling station, fluid is introduced into each of the sampling containers 12, and, after suitable dissolution, a sample fluid is withdrawn therefrom and conducted to a suitable analysis device for testing and/or analysis of the contents of the withdrawn fluid sample. The apparatus 10 is mounted on a suitable base 18 which houses the various pumps, motors, valves, and other controls, etc. for operating and controlling the apparatus 10 for obtaining fluid samples. The sampling apparatus 10 shown in FIG. 1 generally includes a pair of spaced side housings 20 which define therebetween a channel 22 into which sampling containers 12 are loaded and then moved into position. In the preferred embodiment, the plurality of sampling containers 12 are fixedly mounted on a suitable tray 24 which is adapted to be placed in the channel 22 between the spaced side housings 20 and then moved into position. In the embodiment shown in FIG. 1, two trays 24 may be placed in the channel 22 between the side housings 20.

The sampling containers 12 mounted on the trays 24 each include a chamber 26 therein for receipt of fluids and any other substances which are to be mixed or dissolved in the fluids. Preferably, the various sampling containers 12 are mounted on the support tray 24 in a matrix array to provide a series of rows and columns of sampling containers 12. For the sake of the present discussion, a row of sampling containers 12 refers to a set of sampling containers 12 which extends laterally between the upright side housings 20 of the apparatus 10, and a column of sampling containers 12 refers to a set of sampling containers which extends in a longitudinal direction parallel to the channel 22 defined between the upright side housings 20. In the preferred embodiment, each tray 24 includes seven rows and seven columns of sampling containers 12.

The sampling apparatus 10 of the present invention is operative to perform sampling operations with respect to at least one row of sampling containers 12 at any given time, and if desired, to perform sampling operations with respect to a plurality of rows of sampling containers 12. That is, at any given time, the apparatus 10 is operable to perform a sampling operation with respect to each of the seven sampling containers 12 contained in a row of sampling containers 12. If desired, however, the sampling apparatus 10 can also perform sampling operations with respect to seven rows of seven sampling containers each, or 49 sampling containers at a given time.

Figure 3:
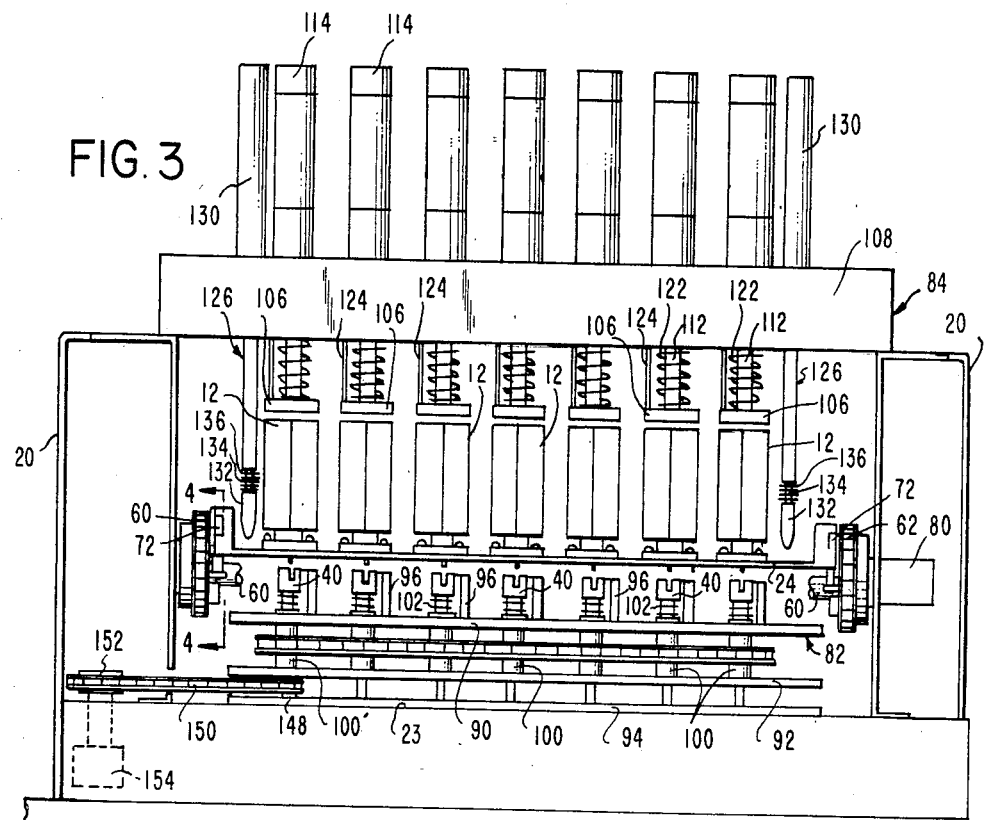
FIG. 3 is a front elevational view of the apparatus shown in FIG. 1, with the covers of the side housings removed.
Figure 5:
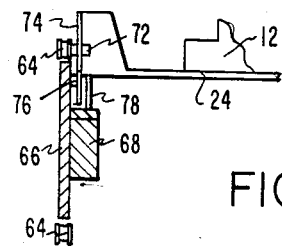
FIG. 5 is a sectional view taken along lines 5—5 of FIG. 4.

Referring now to FIGS. 3, 6, and 7 in particular, each of the sampling containers 12 comprises a generally upright body member having a central bore extending longitudinally from the top end to define a sampling chamber 26 therein. Each of the sampling containers 12 includes an individual agitator or stirrer element 28 mounted in the lower end thereof for agitating materials introduced into the chamber 26. The agitator element 28 preferably includes a series of blades or agitating elements 30 (See FIG. 10) arranged in the lower portion of the chamber 26, the agitating elements 30 being secured to a depending drive shaft 32 which extends downwardly through a bore 31 in the lower portion of the container 12. A bushing 34 is provided in the bottom of the sampling container 12 for positioning the drive shaft 32, and an O-ring or other suitable sealing member 36 is provided for sealing the chamber 26 against leakage through the bore 31. The end of the drive shaft 32 extends outwardly from the bottom of the container 12, and includes a transversely extending pin 38 which is used to couple the drive shaft 32 to a rotatable drive member 40, to be described more fully hereinbelow.

The bore defining the chamber 26 includes a shoulder 42 in the bottom thereof, above the location at which the agitating element 28 is positioned, for supporting a screen member 44. The screen member 44 serves to prevent contact between the agitating element 28 and the tablet or other material form 46 placed in the chamber 26 for dissolution in the dissolution fluid introduced into the chamber 26. A shoulder 48 is also provided adjacent the upper end of the sampling container 26 for supporting a filter member 50 for filtering sample fluid withdrawn from the sampling container 12 during operation.

A fluid inlet channel 52 is provided in the container 12 which extends upwardly from the lower surface of the sampling container 12 and which communicates with a transverse bore 54 in the side of the container 12 for introduction of fluid into the lower portion of the chamber 26 at the elevation of the agitating element 28. A suitable inlet fitting 56 is threadably secured in the inlet channel 52 for providing a suitable connect/disconnect for mating with an inlet conduit means for introduction of dissolution fluid into the chamber 26. A longitudinally extending bore 58, of a smaller diameter than the inlet channel 52, extends from the upper surface of the container 12 downwardly into communication with the transversely extending inlet bore 54, for providing the capability of recycling or recirculating fluid into the chamber 26, as discussed more fully hereinbelow.

Each of the sampling containers 12 is mounted on the container transport tray 24 in a suitable manner, such as by threaded fasteners extending through appropriate openings in the tray 24 into the bottom of the sampling containers 12, so that the drive shafts 32 of the agitating elements 28 and the inlet fittings 56 extend below the lower surface of the tray 24, as best seen in FIG. 6.

The container tray 24 with the plurality of sampling containers 12 thereon is loaded into the sampling apparatus 10 at one end and is then moved longitudinally between the side housings 20 to position a row of containers 12 at the sampling station. Suitable guide means are provided for supporting the lateral edges of the container tray 24 and for guiding it during movement through the apparatus 10. More particularly, in the preferred embodiment, laterally extending shafts 60 are provided at the input and output ends of the channel 22 between the side housings 20. Toothed gears 62 are mounted on the shafts 60 for driving a pair of drive chains 64 trained thereabout, the drive chains 64 extending the length of the housings 20 and each being located adjacent the inner surfaces of the side housings 20. A chain guide rail 66 is suitably secured to the inner surfaces of each side housing 60 for supporting and guiding the upper portions of the chains 64 at the proper elevation. Movable tray guide rails 66 are mounted inwardly of each chain guide rail 66 for limited upward and downward vertical movement relative to the chain guide rails 66. The upper surface of the tray guide rail preferably includes a suitable low friction material to provide for relative free sliding movement of the tray 24 therealong.

Figure 4:
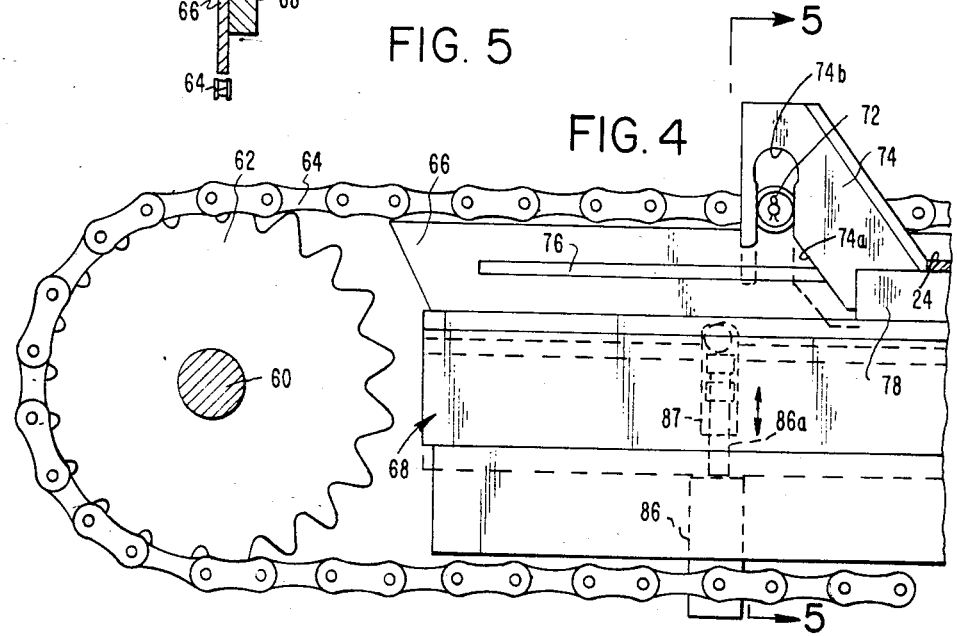
FIG. 4 is a partial side sectional view taken along lines 4—4 of FIG. 3 illustrating how the tray of sampling containers is supported by the apparatus and moved relative thereto.

The drive chains 64 each include laterally protruding bushings or roller members 72 at appropriate spacings along the length thereof so as to receive hook members 74 provided on the forward and rearward ends of the tray 24. The hook members 74, best shown in FIG. 4, include a beveled section 74a which serves to guide the roller members 72 into the slotted portion 74b of in the hook member 74 to provide for relatively precise positioning of the tray 24 relative to the drive chains 64. The chain guide rails 66 preferably include laterally extending lips or flanges 76 which engage the sides of the hook members 74 on the tray 24 to precisely laterally position the tray 24 between the side housings 20. Support pads 78 made of a suitable antifriction material are mounted at the forward and rearward ends of the tray 24 adjacent the hook members 74, and serve to support the tray 24 on the movable guide rails 68 for sliding movement relative thereto. Thus, as the drive chains 64 are driven forwardly, the roller guides 72 in the slotted portions 74b of the hook members 74 serve to pull and push the tray 24 forwardly along the tray guides 68 and thus relative to the side housings 20. The chains 64 may be driven in any suitable manner, such as for example by means of a pneumatically or hydraulically driven piston 80 connected through a one-way clutch to one of the shafts 60. In this manner, suitable forward indexing of the drive chains 64 may be precisely controlled, the amount of movement during each indexing step corresponding to the spacing between adjacent rows of sampling containers 12 on the tray 24.

The elevation of the tray guide rails 68 in their normal position is such as to insure that the sampling containers 12 and trays 24 will pass freely between the lower and upper seal assemblies 82, 84, to be described more fully hereinbelow, which are suitably mounted on the apparatus 10. The relative positioning of the tray 24 and sampling containers 12 in this position with respect to the lower and upper seal assemblies 82, 84 can best be seen in FIG. 6. When the sampling containers 12 are positioned at the sampling station, the tray guide rails 68 are lowered to thereby lower the tray 24 onto the lower seal assemblies 82. This lowering of the tray guide rails 68 is accomplished in the preferred embodiment by means of suitable hydraulic solenoids 86 fixedly mounted in the side housings 20 and having the piston 86a thereof connected to the guide rails 68 (see FIG. 4). Each of the guide rails 68 is mounted in this fashion with the use of two such hydraulic solenoids 86, one at the forward end and one at the rearward end. By retracting the pistons 86a thereof, the guide rails 68 are moved to their lower position (shown in dotted outline in FIG. 4), whereas when the pistons 86a are extended the guide rails 68 are positioned in their upper position. In this regard, the chain guide rails 66 include suitable vertically extending slots 87 through which the connections between the tray guide rails 68 and the pistons 86a of the hydraulic solonoids 86 pass. It will be noted that when the tray guide rails 68 are in their lowered position, the guide bushings 72 on the drive chains 64 are positioned in the upper ends of the slotted section 74b of the hook members 74 on the tray 24.

Lower seal assemblies 82, one for each row of sampling containers 12 to be used at any given time during a sampling operation, are suitably mounted on a support plate 23 extending between the side housings 20. Similarly, corresponding upper seal assemblies 84, one for each lower seal assembly 82, are mounted on the upper ends of the side housings 20. The upper and lower seal assemblies 84, 82 each extend laterally between the side housings 20 and are mounted so as to be in precise alignment with one another to thereby define a series of sampling stations, one for each row of sampling containers 12 to be used during a sampling operation.

As noted above, the sampling apparatus 10 of the present invention is operable to perform sampling operations with respect to the seven rows of containers 12, or 49 containers 12 in total, at any given time. This is accomplished by providing seven lower seal assemblies 82 and seven upper seal assemblies 84, the spacing between the sets of seal assemblies 82, 84 corresponding to the spacing of containers 12 mounted on the tray 24. Of course, fewer sets of seal assemblies 82, 84 could be provided or, if additional rows of containers 12 are mounted on a tray 24, a larger number of seal assemblies 82, 84 could be utilized, thereby increasing the number of sampling containers 12 which can be used at a time. As each set of lower and upper seal assemblies 82, 84 are substantially identical, only one set of such assemblies 82, 84 will be described hereinbelow. The function of the upper and lower seal assemblies 84, 82 is to couple input and output fluid conduits 14, 16 with the inlet channels 52 and the open upper ends of the sampling containers 12 to provide for the introduction of fluid into the chambers 26 and the withdrawal of fluid sample from the chambers 26. In addition, the upper and lower seal assemblies 84, 82 also serve to seal the inlet channel 52 and the upper open end of each of the containers 12 in order to prevent the possibility of leakage during a sampling operation.

As best seen in FIGS. 3, 6 and 7, each lower seal assembly 82 includes three vertically spaced plates 90, 92, 94 suitably interconnected together. On the upper plate 90 there is mounted a plurality of fluid inlet blocks 96 to which appropriate fluid inlet conduits 14 are coupled on the sides thereof. The inlet blocks 96 each include a channel therein for conducting fluid from the inlet conduit 14 thereof to the upper end of the block 96. Suitable gaskets or seal members 98 are provided on the upper surface of the blocks 98 about the exit ends of the fluid channels therein. The series of fluid inlet blocks 96 are suitably secured on the top plate 90 of the lower seal assembly 82 so that the exit ends thereof are in alignment with the passageways through the inlet fittings 56 of a row of sampling containers 12 when the row of sampling containers 12 are positioned at the sampling station. In other words, the blocks 96 are positioned on the top plate 90 of the lower seal assembly 82 and the same spacing as the sampling containers 12 in a row of containers 12 on the tray 24. In terms of the embodiment shown in the figures, the blocks 96 are located on the rearward side and slightly to the right of the center line of each of the sampling container positions.

Also mounted on the upper plate 90 of the lower seal assembly 82 are a plurality of coupling drive bushings 40 for coupling the agitator drive shafts with a suitable drive mechanism for rotating each of the agitator drive shafts 32 in the row of sampling containers 12. More particularly, each coupling drive bushing 40 is slidably mounted on a rotatable drive shaft 100 for rotation therewith. The rotatable drive shafts 100 in turn are rotatably mounted between the middle plate 92 and the upper plate 90 of the lower seal assembly 82. A biasing spring 102 is also mounted on each rotatable drive shaft 100 and in engagement with the drive bushing 40 thereon for urging same upwardly. The drive bushing 40 includes a pair of spaced slots 104 extending from the upper surface thereof for receipt of the transverse pin 38 on an agitator drive shaft 32 to thereby rotationally couple the agitator shafts 32 to corresponding rotational dirve shafts 100. The series of drive bushings 40 and drive shafts 100 are suitably arranged on the lower seal assembly 82 so as to be in alignment with the agitator drive shafts 32 of the sampling containers 12 contained in the row of containers 12 positioned at the sampling station.

Each upper seal assembly 84 includes a suitable coupling/sealing cover member 106 which is adapted to seal the upper ends of the sampling containers 12 positioned in a row at the sampling station and to provide fluid communication between the interior of the chambers 26 and output conduits 16 during a sampling operation. In the preferred embodiment, the upper seal assembly 84 includes a suitable cross support member 108 extending between the side housings 20 and carrying thereon the plurality of coupling/sealing cover members 106 for making sealing contact with the upper ends of each of the sampling containers 12 in alignment therewith. A suitable gasket or sealing member 110 is provided on the lower surfaces of the cover members 106. The cover members 106 are each generally rectangular in shape and are each carried by the shaft 112 of a suitable actuating device 114 mounted on the cross support member 108. The actuating devices 114, which may for example comprise pneumatic cylinders, are operable to move the respective cover members 106 downwardly and into sealing engagement with the upper open ends of the sampling containers 12 when the row of containers 12 is positioned at the sampling station.

In the preferred embodiment, the cover members 106 are each mounted so as to provide an essentially floating head arrangement therefor. This may be accomplished by providing an enlarged bore 116 in the upper end of the cover member 106 into which the end of the shaft 112 protrudes and is connected thereto by a transversely extending pin 118. An enlarged transverse opening 120 is provided in the cover member 106 for receipt of the pin 118 so that limited universal movement of the cover member 106 relative to the end of the shaft 112 is provided. In other words, the cover members 106 are able to "rock" or tilt slightly with respect to the shafts 112. The cover members 106 are each spring loaded by means of a spring 122 interposed between the cover member 106 and the lower surface of the cross support member 108 for the upper seal assembly 84. An anti-rotation pin 124 is also provided for each cover member 106 which extends upwardly from the cover member 106 into a suitable opening in the lower surface of the cross support member 108 to prevent substantial rotation of the cover member 106 relative to the cross support member 108. Again, however, some play is permitted so as to provide essentially limited universal movement of the cover members 106. This arrangement is most advantageous in order to insure that a level and flush mating is provided between the lower surface of the cover members 106 and the top surface of the respective sampling containers 12. If the cover members were held in fixed position and if precise alignment between the cover members and the sampling containers were not provided, leakage of fluid out of the sampling containers 12 might occur. Essentially, with the floating head type arrangement for sealing the top of the sampling containers 12, a uniform pressure over the sealing surface of the gasket 110 will be provided, thereby improving the seal strength and life of the cover members 106.

In operation, the tray 24 of sampling containers 12 is moved into position so that one row of sampling containers 12 is in alignment with a set of lower and upper seal assemblies 82, 84. If a plurality of sets of assemblies 82, 84 are provided, the tray 24 is moved so that a row of containers 12 is in alignment with each set of assemblies 82, 84. Once the tray 24 is in position, the hydraulic solenoids 86 are actuated to move the tray guide rails 68 downwardly to thereby lower the tray 24 onto the lower seal assembly or assemblies 82 with the desired row or rows of sampling containers 12 in alignment therewith.

In order to aid in alignment of the sampling containers with the respective fluid inlet blocks 96 and drive bushings 40, guide pins 126 are provided on the upper seal assembly or assemblies 84 which are adapted to engage guide holes 128 on the tray 24 to properly position the tray 24 with respect to the lower and upper seal or assemblies 82, 84. More particularly, after the tray 24 has been lowered, guide pin actuating means 130, such as pneumatic cylinders, are actuated to move the guide pins 126 downwardly into engagement with the upper surface of the tray 24. Any misalignment between the tray 24 and the respective lower seal assemblies 82 will be corrected by virtue of the guide pins 126 passing through the guide openings 128 in the tray 24 and thereby repositioning the tray 24 precisely into the proper orientation. In this regard, as best seen in FIGS. 3 and 6, the guide pins 126 each include a spring biased lower section 132 mounted to the shaft 134 of the actuating means 130, such as for example a pneumatic cylinder, supported by the support member 108. A spring 136 is provided for biasing the lower section 132 away from the shaft 134. The lower section 132 of each guide pin 126 has a generally tapered configuration so as to insure insertion of the end of the guide pin 126 into the guide holes 128 on the tray 24 once the tray 24 has been moved generally into position at the sampling station. That is, when the tray 24 has been moved into position, the guide pin actuating means 130 are actuated and the guide pins 126 moved downwardly to engage the tray 24. In view of the smaller diameter of the end of the guide pin 126, and the fact that the sampling containers 12 are in rough alignment with the upper and lower seal assemblies 84, 82, the guide pins 126 will pass through the guide holes 128 and precisely align the tray 24 having the sampling containers 12 thereon with the upper and lower seal assemblies 84, 82. In the preferred embodiment, two guide pins 126 are provided and are mounted at the lateral ends of each upper seal assembly 84. However, a greater number or lesser number of guide pins 126 could be provided to satisfy the requirement of precise horziontal positioning of the tray 24 with respect to the upper and lower seal assemblies 84, 82. It will thus be appreciated that this arrangement insures proper positioning of the sample containers 12 with respect to the sealing assemblies 82, 84 each time the tray 24 is moved or indexed forward.

It should further be noted that when the tray 24 is lowered onto the lower seal assembly or assemblies 82, the drive shafts 32 of the individual agitating elements 28 will be in alignment with and received within the upper ends of the respective drive coupling bushings 40.

In this regard, the diameter of the drive shafts 32 is preferably less than the diameter of the opening in the upper end of the bushings 40 so as to provide for sufficient tolerances to insure a good mating of the drive bushings 40 with the drive shafts 32, even though the positioning of the sample container tray 24 may not be precise with respect to the lower seal assemblies 82. In other words, by virtue of this arrangement, a significant margin of error is allowed in the positioning of the containers 12 on the tray 24 and in proper positioning of the sampling containers 12 with respect to the upper and lower seal assemblies 84, 82.

It should also be noted that when the tray 24 is lowered onto the lower seal assembly or assemblies 82, the transverse pins 38 on the agitator drive shafts 32 may not necessarily be aligned with the slots 104 in the respective drive bushing 40. However, the tips of the drive shafts 32 will be received within the openings of the drive bushings 40. Also, since the drive bushings 40 are spring loaded upwardly by the springs 102, when the tray 24 is lowered, those drive bushings 40 in which the transversely extending pins 38 are not aligned with the slots 104 will be forced downwardly. Thereafter, as the drive bushings 40 are rotated upon rotation of the drive shafts 100, at most the drive shafts 100 will only make a one-half turn before the slots 104 are brought into alignment with the pins 38. When this occurs, the drive bushings 40 will be moved upwardly by the springs 102 and the agitator shafts 32 rotationally coupled to the drive shafts 100. In other words, as the drive bushings 40 are rotated, at most they will rotate one-half turn before the ends of the transversely extending pins 38 are aligned with and pass into the slots 104 provided therein.

After the tray 24 has been lowered and rests on the lower seal assembly or assemblies 82, the actuating devices 114 for the individual sealing cover members 106 of the upper seal assembly or assemblies 84 are actuated to move the cover members 106 downwardly into sealing engagement with the upper ends of the sampling containers 12 and to clamp each of the sampling containers 12 between respective sealing means 110, 98 on the upper and lower seal assemblies 84, 82. It should be noted that good sealing engagement is insured by virtue of the fact that a separate cover member 106 is provided for each of the sampling containers 12 at the sampling station, the fact that each cover member 106 is separately actuated, independent of the other cover members 106, and the fact that a floating head design is provided for the cover members 106. More particularly, the feature of providing individual and independent sealing cover members 106 allows for a much less precise dimensional compatibility between the sealing cover members 106 and the sampling containers 12. Slight variations in the height of the sampling containers 12, uniformity of the trays 24, uniformity of the mounting of the sampling containers 12 on the trays 24, etc. will not prevent proper functioning of the seals 110. Also, since a clamping type seal arrangement is provided, as opposed to a sliding seal arrangement such as provided in connection with the dissolution cell disclosed in U.S. Pat. No. 4,279,860, there will be less wear on the seal elements 110, 98, and further a more efficient and sound seal for assuring against leakage will be provided.

Another feature of the apparatus 10 in accordance with the present invention which minimizes tolerance requirements is the fact that the inlet openings in the fittings 56 in the inlet channels 52 on the sampling containers 12 are of a larger dimension than the size of the channels provided in the blocks 96 on the lower seal assembly 92. This is advantageous since it insures fluid communication being established between the seal blocks 96 and the inlet channels 52 to the sampling containers 12, even if there is slight misalignment.

Fluid conduits 16 for withdrawing fluid samples from the chambers 26 of the sampling containers 12 are connected to appropriate fittings (not shown) on the upper cover members 106 which engage the top ends of the sampling containers 12 (see FIGS. 6 and 7). The fluid conduits 16 are in communication with openings which extend through the cover members 106 and which are thus in communication with the chambers 26 of the sampling containers 12 when the cover members 106 are in sealing relationship with the sampling containers 12. The location of the connections of the fluid conduits 16 to the cover members 106, and thus of the openings through the cover members 106, is shown in FIG. 8. Fluid samples may thus be withdrawn from the sampling containers 12 through the appropriate openings and then conducted to a suitable testing station (not shown).

The outlet fluid conduits 16 (attached to the cover members 106) and the inlet fluid conduits 14 (attached to the blocks 96) are directed away from the sampling station, such as by passing laterally along or adjacent to the upper and lower seal assemblies 84, 82. The conduits 14, 16 normally are directed into the interior of one of the side housings 20 to be connected to suitable pumps, valves, controls, etc. Because the conduits 14, 16 will pass at roughly the same elevations as the upper and lower seal assemblies 84, 82, the conduits 14, 16 will not interfere with movement of the tray 14.

A separate passageway 140 is provided in each cover member 106 and has a recycle conduit 142 connected thereton. The passageway 140 is designed to be in alignment with the recycle bore 58 provided in the associated sampling container 12 when the cover member 106 is in sealing relationship therewith. As with the lower inlet fluid connection between the blocks 96 on the lower seal assembly 82 and the inlet fittings 56 for the containers 12, the lateral dimension of the passageway 40 in the lower surface of the cover members 106 is of a greater dimension than the dimension of the recycle bore 58 in the sampling containers 12 to insure establishment of fluid communication therebetween for recycling fluid withdrawn from the container 12 even if there is slight misalignment between the sampling container 12 and its respective cover member 106.

Figure 2:
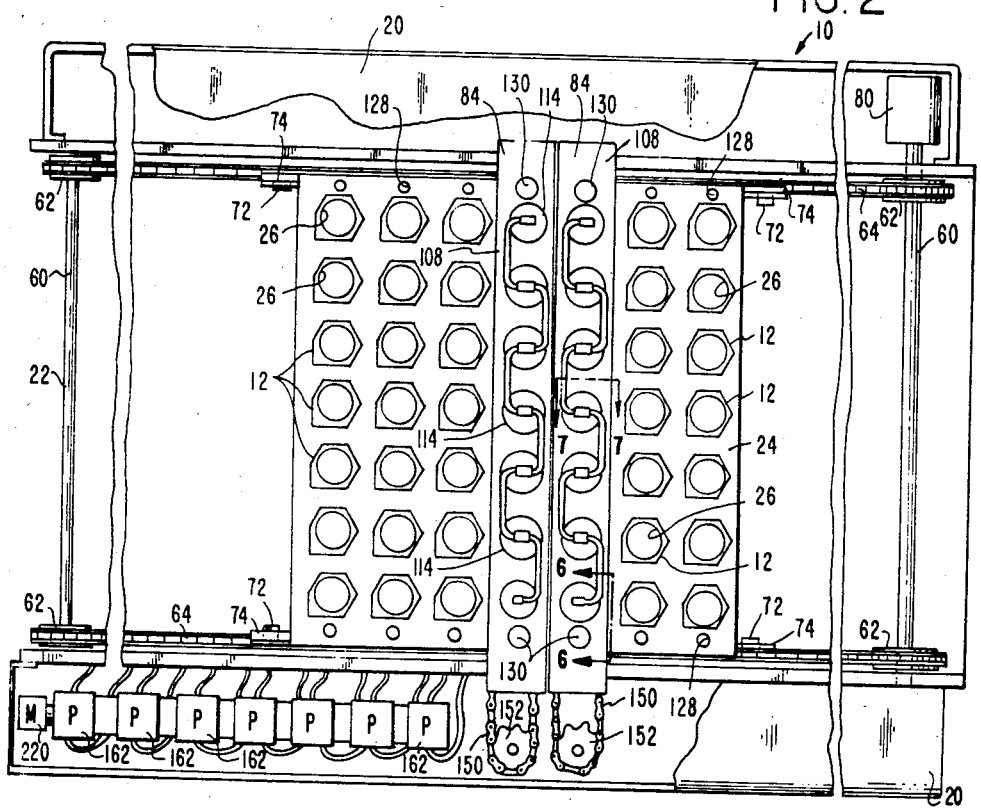
FIG. 2 is a plan view partially broken away, of the apparatus shown in FIG. 1.

In accordance with the present invention, the apparatus 10 is capable of functioning to provide an agitation of the fluid or other substances contained within the sampling containers 12 by virtue of rotation of the individual agitating elements 28 mounted in each of the sample containers 12. Such rotation is accomplished by rotating the drive bushings 40 mounted on the lower seal assembly or assemblies 82. More particularly and as best seen in FIG. 2, in each lower seal assembly 82, the rotatable drive shafts 100 to which the drive bushings 40 are mounted are provided with a gear 144 thereon between the middle and upper plates 90, 92. A drive chain 146 is trained about the gears 144 of the all of the drive shafts 100 of each lower seal assembly 82, i.e., the seven drive shafts 100 in the preferred embodiments, so that when one of the shafts 100' is rotated, the remaining shafts 100 will likewise be rotated. Between the middle plate 92 and the lower plate 94, one of the drive shafts 100' has a second gear 148 secured thereto about which a second drive chain 150 is trained. As best seen in FIGS. 2 and 3, the second drive chain 150 passes laterally outward through one of the side housings 20 and is trained about a drive gear 152. The drive gear 157 is suitably connected to a drive means 154 such as a motor. It will thus be appreciated that when the motor 154 is operated, it will drive the chain 150 to rotate the drive shaft 100' mounted in the lower seal assembly 82, and, by virtue of the chain drive mechanism 144, 146 between all of the drive shafts 100, will rotate the remaining drive shafts 100 of the lower seal assembly 82. As shown in FIG. 2, a separate motor 154 and drive gear 157 may be provided for each lower seal assembly 82, or alternatively, a single motor and drive gear could be provided for driving a drive shaft of a plurality of lower seal assemblies 82. Because of the pin slot 38, 104 interconnection between the drive bushings 40 and the drive shafts 32 on each of the agitating elements 28, when the motor 154 is actuated, the agitating elements 28 in each of the sampling containers 12 will be rotated to agitate the fluid in the containers 12.

Figure 9:
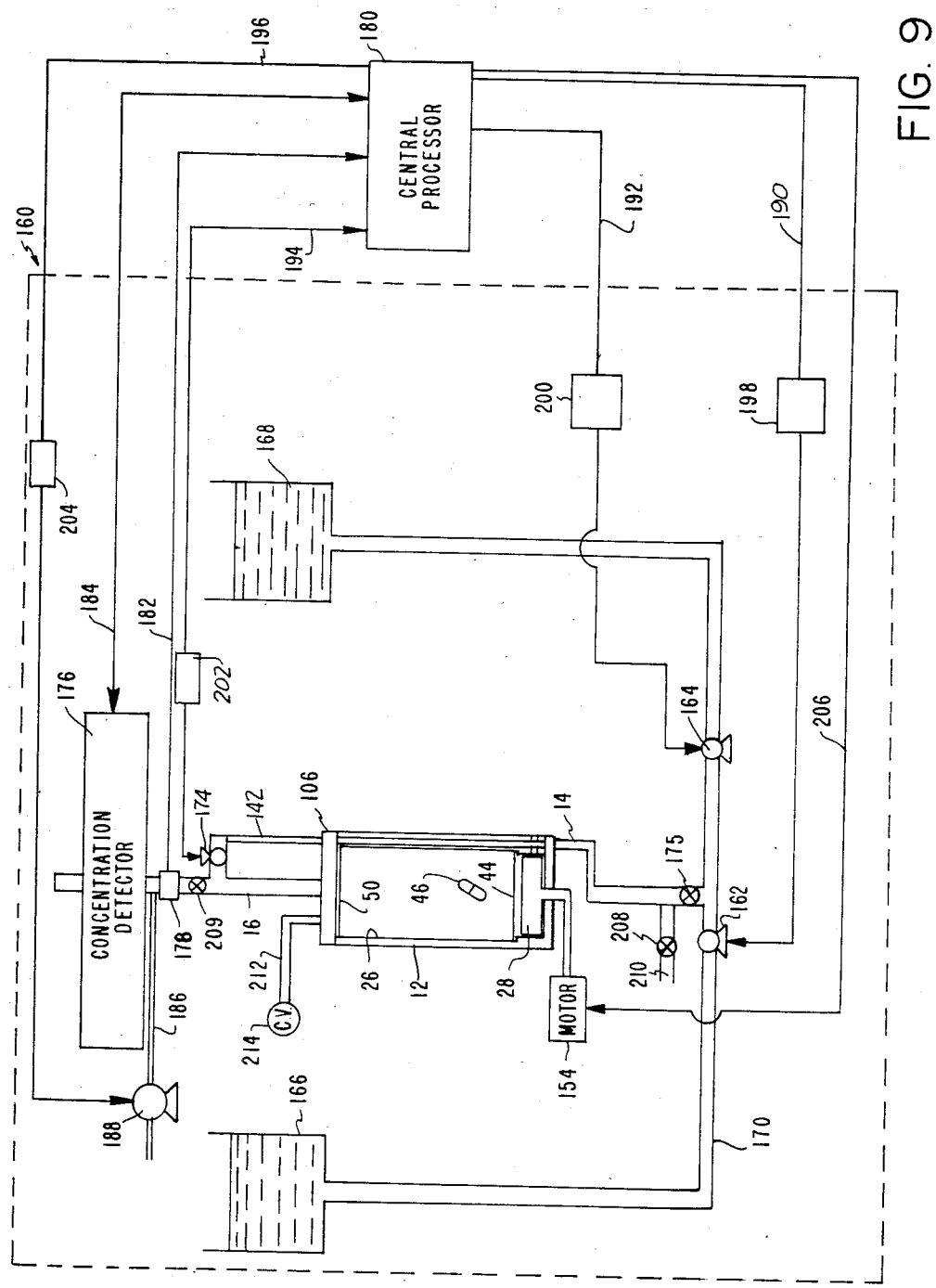
FIG. 9 is a schematic diagram illustrating the use of the apparatus of the present invention in a dissolution testing system.

When the upper and lower seal assemblies 84, 87 have been coupled and sealed to a row or rows of sampling containers 12, fluid may be introduced into the chambers 26 of the containers 12 and fluid samples withdrawn therefrom and conducted to a suitable testing or analysis apparatus. In this regard, as noted hereinabove, the sampling apparatus 10 in accordance with the present invention is particularly useful in connection with a dissolution testing apparatus 160. FIG. 9 illustrates schematically the functioning of the sampling apparatus 10 for one sampling container 12 in connection with such a system 160. However, it will be appreciated that because a plurality of sampling containers 12 are moved simultaneously at one time into position at the sampling station and coupled to individual input and output conduits 14, 16, the dissolution testing process illustrated in FIG. 9 will be performed with respect to a plurality of sampling containers 12, e.g., seven in accordance with the particular embodiment shown and described hereinabove.

Referring now to FIG. 9, there is shown a block diagram of an automatic flow through dissolution testing system 160 in which the sampling apparatus 10 of the present invention may be used. For simplicity, the various elements illustrated therein are not shown to scale. The overall dissolution testing system 160 comprises a plurality of sampling containers or cells 12, one of which is shown in FIG. 9, in which specimens of drug products 46 undergoing evaluation are positioned. Each sampling container 12 includes a filter membrane 50 mounted in the upper end thereof and a filtering screen element 44 provided in the lower end thereof above the agitating element 28. Dissolution liquid or media is introduced into the sampling container 12 via an input line 14 under the influence of suitable pumps 162, 164. A separate input line 14 is provided for each sampling container 12. In the preferred embodiment, two reservoirs 166, 168 are provided containing supplies of first and second dissolution media, for example an acid medium and an alkaline medium. Each of the dissolutioned medias are suitably connected through appropriate fluid conduits 170, 172 to the individual input media lines 14. Separate lines 170, 172 are provided from the sources 166, 168 of dissolution media for each of the separate sampling containers 12 in use at one time. Pumping devices 162, 164 are provided in each of the separate dissolution media lines 170, 172 for driving fluid into the sampling container input line 14 and from there into the chamber 26 of the sampling container 12. Check valves may be provided in each of the individual media lines 170, 172 for preventing back or cross flow of the various dissolution media. Also, a valve 174 is provided in the input media line 14 for controlling introduction of the dissolution media into the containers 12. Suitable controls are also provided for varying the relative proportions of each of the dissolution media to be introduced into the sampling containers.

A fluid sample is conducted from each sampling container 12 through an output line 16. A recirculation line 142 having a recirculation pump 176 therein is provided for carrying a portion of the withdrawn fluid sample from the line 16 and for reintroducing same into the container 12 through the recycle bore 58 provided in the container 12. The recycle bore 58 communicates with the transverse inlet bore 54 so that recycled fluid is introduced into the container 12 adjacent the position of the agitating element 28. The portion of the withdrawn sample fluid which is not recirculated is conducted via the output line 16 to a suitable concentration detector or other analysis device 176 as may be desired. A flow transducer 178 is provided in the output line 16 for providing a quantitative measurement of the liquid flow rate. Information from the transducer 178 may be transmitted via line 182 to a suitable central processor or unit 180 for controlling operation of the input pumps 162, 164. The concentration detector 176, which for example may comprise a spectrophotometer, provides periodic or continuous measurement of the drug concentration in the output flow line 16. This information may be transmitted to the central processor unit via line 184. Of course, other types of measurements and tests may be performed on the fluid sample output of the system 160 for each of the sample containers 12. Further, a dilution line 186 having a pump 188 therein may be provided in communication with the output line 16 for introducing dilution fluid into the output in order to provide a meaningful and readable measurement of the concentration, if desired.

The pumps 162, 164, 177, and 188 are all preferably of a positive displacement type, such as for example peristaltic pumps, which are capable of producing precisely controlled flow rates. The central processor unit 180 may provide control for this purpose by appropriate signals through lines 190, 192, 194, and 196 which modulate the excitation of the pumps through the use of appropriate pump speed modulators 198, 200, 202, 204. Also, control of the various valves 175, 208 and 209 may be provided by the central processor unit 180. The central processor unit 180 may in addition provide appropriate control signals via line 206 for actuating the motor 154 to rotate the individual agitating elements 28 in each of the sampling containers 12, as well as for controlling indexing of the tray 24 of sampling containers 12 forwardly to align additional rows of sampling containers 12 with the upper and lower seal assemblies 84, 82. Such control functions are well known in the art, and therefore need not be described in detail herein as they do not perform an intrinsic part of the present invention.

After a sampling operation has been completed, fluid contained in the containers 12 may be withdrawn by closing valve 174 and opening a valve 208 in a drain line 210. The drain line 210 may be connected to a suitable source of vacuum to withdraw fluid from the container 12. In this regard, an air bleed line 217 containing a check valve 214 therein may also be provided for aiding in assisting the emptying of the sampling containers 12. The bleed line 217 is connected to the upper end of the container 12 through an appropriate opening in the cover member 106 therefor (see FIG. 8). The check valve 214 in the air bleed line 217 is arranged so as to permit air to be drawn into the container 12 when the valve 208 in the drain line 210 is opened, and to prevent fluid from passing out of the container 210 through the line 212. Exit valve 209 prevents syphoning or evacuation of line to detector and waste.

Thus, it will be appreciated that in accordance with the present invention, there is provided a sampling apparatus 10 for efficiently producing a plurality of fluid samples. The apparatus 10 may be used in connection with a wide variety of systems in which fluid samples are to be obtained and then analyzed for certain properties contained therein. The sampling apparatus 10 may be used to obtain fluid samples either continuously or periodically on a substantially automated basis. A plurality of sampling containers 12 are provided in the apparatus 10 which are moved substantially simultaneously into position at a sampling station, and input and output fluid conduits 14, 16 coupled thereto for the introduction and withdrawal of fluid from the plurality of containers 12, the coupling of the fluid conduits 14, 16 being accomplished in a manner to insure that the containers 12 are sealed against fluid leakage during operation. In accordance with the preferred embodiment, the sealing of the containers 12 is accomplished by providing individual sealing means 96, 98, 106, 110 for the input and output openings 52, 26 in the containers 12 with which the input and output conduits 14, 16 are in fluid communication. Preferably, clamping type sealing arrangements are provided, as opposed to sliding type sealing arrangements, in order to insure complete and effective sealing to prevent fluid leakage.

Another advantageous feature in accordance with the present invention is the provision of individual agitating means 28 provided in each of the sampling containers 12, thereby permitting the obtainment of properly agitated fluid samples from a plurality of containers 12 during any one sampling operation. This is advantageous in that coupling of agitating elements 28 with the sampling containers 12 in an effective, sealed arrangement is not neccesary. Also, the provision of individual agitating elements 28 is advantageous in connection with cleaning and sterilizing the equipment after use. More particularly, it will be appreciated that after a sampling operation has been performed, the tray 24 containing the sample containers 12 may simply be removed from the apparatus 10 and efficiently and thoroughly cleaned and sterilized while the apparatus 10 is utilized in connection with obtaining additional fluid samples from containers 12 provided on another tray 24. This thus greatly enhances flexibility and operation of the apparatus 10. Furthermore, automatic clean out posses the potential problems of carry-over and contamination of the next test.

A still further feature in accordance with the apparatus 10 of the present invention is the fact that each set of pumps 162, 164, 174, 188 utilized in the apparatus 10 may be driven by a common drive means, thereby assuring uniformity of operating conditions in terms of the introduction of different fluid media, the withdrawal of fluid samples and the conditions under with the fluid samples are obtained. For example, as illustrated in FIG. 2, one set of pumps, for example pumps 162 for controlling introducing of fluid media from one of the sources 166 into the containers 12, may be arranged adjacent to one another so as to be driven by a common drive device, such as a motor 220. In this manner, each of these pumps 162 may thus be driven at a constant speed, thereby assuring that there is a uniform introduction of the same amount of fluid media from the common source 166 into each of the sampling containers 12 being used at a given time. Each of the different sets of pumps 162, 164, 174, 188 (i.e., the set of pumps 162 for controlling introduction of fluid media from the first source 166, the set 164 for controlling introduction of fluid media from the second source 168, the set 174 for controlling recycle flow, and the set 188 for controlling introduction of dilution media) used in the apparatus 10 could be driven by a respective common drive device so that uniform conditions and operation in the system will be provided. Furthermore, it will be appreciated that when sampling operations are performed with respect to a plurality of rows of sampling containers 12, different sets of flow conditions can be provided for each of the different rows of sampling containers 12 through the use of separate common drive devices for controlling the sets of pumps 162, 164, 174, 188 for each different row of sampling containers 12. This also greatly enhances the flexibility and use of the apparatus 10.

Figure 10:
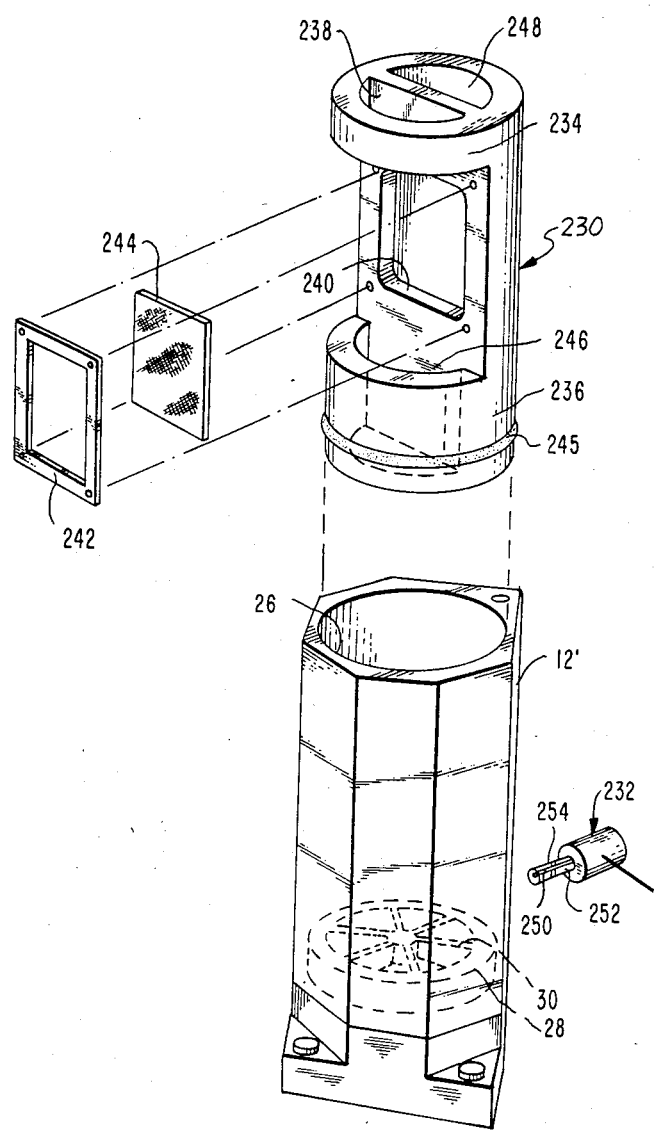
FIG. 10 is an exploded perspective view showing assembly of an insert member into a sampling container, the insert member being useful in connection with conducting permeability tests.

Another feature providing greater flexibility of the sampling apparatus 10 in accordance with the present invention is illustrated in connection with FIG. 10 which shows an exploded perspective view of an insert member 230 and sampling container 12' which is useful in connection with conducting membrane permeability testing. The sampling container 12' substantially corresponds to the sampling container 12 illustrated and described hereinabove with the exception that an additional bore (not shown) is provided for a valve member 232 to be inserted, the purpose of which will be discussed more fully hereinbelow. The insert member 230 has a cross sectional shape and configuration susbstantially corresponding to the cross sectional shape and configuration of the bore defining the chamber 26 in the sampling container 121. In the preferred embodiment, the bore is of a circular cross sectional shape, and consequently in the insert member 230 has a generally cylindrical configuration.

The insert member 230 includes upper and lower cylindrical sections 234, 236 and a central longitudinally extending wall section 238. The wall section 238 includes a window or passageway 240 therethrough and a clamp member 242 is provided for mounting to the wall section 238 surrounding the passageway 240 to hold a membrane 240 in place on the wall section 238 of the insert member 230. One-half of the sidewall of the insert member 230 is open to facilitate mounting of the clamp member 242. When the insert member 230 is inserted into the sampling container 12', the central wall section 238 will thus serve to divide the chamber 26 into two subchambers 246, 248 separated by the membrane 244 mounted in the wall section 238. Suitable seals, such as for example O-rings 246, may be provided for sealing and holding the insert member 230 in place. The upper cylindrical section 234 is in open communication with each of the two subchambers 246, 248 formed therein, and the lower cylindrical section 236 of one of the chambers 246 is open while the other one 248 is closed.

Thus, communication with the area occupied by the agitator element 28 will only be provided with respect to one of the subchambers 246. Because the bottom of the other chamber 248 is closed, any fluid introduced into the sampling container 12' will only flow through the first chamber 246. Outlet lines will be coupled with respect to the top cover member 106 on the upper seal assembly 84 so as to be in communication with each of the respective chambers 246, 248. In this regard, it will be noted with reference to FIG. 8 that the cover member 106 includes a pair of passageways (one for each flow conduit 16 and 212) which will be in communication with the chamber 26 in the sampling container 12 when coupled thereto. Thus, by appropriately positioning the insert member 230 in the chamber 26 of the sampling container 12', and modifying the flow lines 212, 16, fluid communication with each of the subchambers 246 may be provided. Thus, in this manner, the permeability of the introduction fluid across the membrane 244 can be measured by determining the concentration of the solution in the second chamber 248.

If desired, fluid may be introduced into the second chamber 248 via a suitable modification to the sampling container 12'. Specifically, a bore (not shown) is provided through the wall of the sampling container 12' in alignment with the recycle liine 58, and is fitted with a valve 232. In one position, the valve 232 blocks normal return of the recycle line 58 into the inlet channel 52 and redirects the flow into the second chamber 248 via a slot 250 in the surface of the stem 252 of the valve 232. In another position, the valve 232 allows communication of flow from the recycle line 58 with the inlet channel 52 via a port 254 provided in the stem 252. In a still further position, the valve 232 blocks off the flow entirely. This type of arrangement thus provides for independent recirculating of the fluid in the second chamber 248 through the use of the recycle pump 174 and further provides for some mixing of the fluid in both chambers 246, 248.

The use of such an insert member 230 is most advantageous in conducting membrane permeability testing and analysis. Specifically, with the insert member 230, diffusion frame or through a fixed member 242 (which may for example comprise excised human or mouse skin) into a fluid, or diffusion from one solution or suspension into another may be tested. As can be appreciated, the insert member 230 thus provides a great deal of flexibility for testing and analysis of transdermal or transmembrane permeability processes.

A still further feature of the sampling containers 12 of the present invention is the fact that they are readily adapted so as to be capable of using a standard dosage form basket (not shown) which can be attached directly to the agitator element 28 in an inverted configuration with the dosage form 216 being placed into the basket. The utility of the basket is several fold. For example, the basket comprises a mesh screen which is of a much larger surface area than the filter 50 at the normal exit of the sampling container 12. In a study of a formulation which causes blockage of the filter 50, the dosage form 46 may thus be placed in the basket and the basket screen area, being much larger than the cross sectional area of the top of the chamber 26 in the containers 12, can collect more particulate matter and prevent plugging of the filter 50. Another utility of the standard dosage form basket is to keep capsules or other low density dosage forms 46 from floating to the top of the sampling containers 12 to thereby insure that the dosage forms are exposed to proper conditions of agitation. The basket in being attached to the stirrer or agitating element 28 thus will circulate at the same rate as does the stirrer 28 itself, much in the manner that a USP dissolution basket apparatus rotates.

While the preferred embodiments of the present invention has been shown and described, it will be understood that such are merely illustrative and that changes may be made without departing from the scope of invention as claimed.

What is claimed is:

1. Sampling apparatus for obtaining a plurality of fluid samples, comprising:

a plurality of sampling containers each having a chamber therein for receipt of a fluid, each of said sampling containers including openings for communication with fluid conducting means, each of said openings extending in a first direction;

drive means for simultaneously moving said plurality of sampling containers to a sampling station;

first fluid conducting means for each of said sampling containers for conducting a fluid into each of said sampling containers when said sampling containers are positioned at said sampling station;

second fluid conducting means for each of said sampling containers for withdrawing a fluid sample from each of said sampling containers when said sampling containers are positioned at said sampling station; and coupling means located at said sampling station for coupling said first and second fluid conducting means with said chambers of each of said sampling containers when said sampling containers are positioned at said sampling station, said coupling means including sealing means for individually sealing said chamber of each of said sampling containers when said first and second fluid conducting means are coupled to said sampling containers, said coupling means comprising moving means for moving said first and second fluid conducting means into fluid communication with said openings in said sampling containers, said moving means comprising means for moving said first and second fluid conducting means in said first direction and for applying a force along said first direction with respect to each of said sampling containers to clamp each of said sampling containers and its associated first and second fluid conducting means together to seal said openings.

2. The sampling apparatus of claim 1 wherein said openings in each of said sampling containers are disposed at opposite ends of each said sampling container, and wherein said moving means clamps each of said sampling containers between its associated first and second fluid conducting means.

3. The sampling apparatus of claim 1 wherein one of said openings in each of said sampling containers comprises an open top end of said sampling containers; wherein said coupling means further includes individual cover members for each of said sampling containers for covering said open top end, and said moving means comprises means for moving each of said cover members in said first direction toward said open top end of its associated sampling container and for applying a force to each said cover member to clamp said cover member to said open top end of its associated sampling container in sealing relationship therewith when said cover member has been moved into engagement with said open top end; and wherein at least one of said first and second fluid conducting means associated with each of said sampling containers is supported by its associated cover member and communicates with said chamber of said associated sampling container through said associated cover member.

4. The sampling apparatus of claim 3 wherein said moving means comprises an actuating member for each of said sampling containers, each of said actuating members having a rod to which one of said cover members is mounted for limited universal movement, and each of said actuating members being operative to move its associated cover member into engagement with its associated sampling container to ensure effective sealing engagement of said cover members with said associated sampling containers.

5. The sampling apparatus of claim 4 wherein the other of said openings in each of said sampling containers is located in the bottom end of said sampling containers; wherein said coupling means further includes bottom seal means for engaging at least a portion of the bottom end of said sampling containers about said opening therein; and wherein the other of said first and second fluid conducting means associated with each of said sampling containers is mounted on said bottom sealing means and communicates with said opening in said bottom end of said associated sampling container through said bottom seal means.

6. The sampling apparatus of claim 5 wherein said moving means applies a force to clamp each of said sampling containers between its associated cover member and said bottom sealing means when said actuating members move said cover members into engagement with said associated sampling containers.

7. The sampling apparatus of claim 6 further including a support tray on which each of said plurality of sampling containers is mounted, and wherein said drive means comprises means for driving said tray to position said sampling containers at said sampling station.

8. The sampling apparatus of claim 7 wherein said tray includes alignment openings therethrough, and wherein said apparatus further includes guide pins for said alignment openings and guide pin moving means for inserting said guide pins into said alignment openings to align said sampling containers with respect to said associated cover members and said bottom seal means, said guide pin moving means being operative after said sampling containers are moved to said sampling station and before actuation of said actuating means.

9. The sampling apparatus of claim 7 wherein said drive means is operative to move said tray in a direction perpendicular to the direction in which said actuating members move said cover members.

10. The sampling apparatus of claim 7 further including support means for stationarily supporting said bottom seal means at said sampling station; wherein said drive means includes tray support means for supporting said tray at an elevation above said bottom seal means as said drive means moves said tray toward said sampling station; and wherein said actuating members are operative to position said cover members at an elevation above said open top ends of said sampling containers as said drive means moves said tray toward said sampling station.

11. The sampling apparatus of claim 10 wherein said drive means further includes tray moving means for lowering said tray relative to said bottom seal means to position said bottom ends of said sampling containers on said bottom seal means after said sampling containers are moved to said sampling station; and wherein said actuating members are each operative to move said associated cover members toward said open top ends of said associated sampling containers to clamp each of said sampling containers between said bottom seal means and said associated cover members after said tray has been lowered.

12. The sampling apparatus of claim 11 wherein said tray support means comprises guide rails along which said tray is moved by said drive means, and wherein said tray moving means comprises means for lowering said guide rails relative to the bottom seal means.

13. The sampling apparatus of claim 10 wherein said sampling containers are arranged in a transverse row on said tray, said transverse row of sampling containers extending in a direction perpendicular to the direction of movement along which said drive means drives said tray.

14. The sampling apparatus of claim 13 wherein said plurality of sampling containers comprises a first plurality of sampling containers arranged in a first transverse row on said tray, and said apparatus further including a second plurality of sampling containers arranged in a second transverse row on said tray, each of said sampling containers in said second transverse row being in alignment with one of said sampling containers in said first transverse row.

15. The sampling apparatus of claim 14 wherein said cover members and said bottom seal means are each arranged in a transverse row extending perpendicular to said direction of movement of said tray.

16. The sampling apparatus of claim 15 wherein said cover members comprise a first set of cover members; wherein said bottom seal means comprises first bottom seal means; and said apparatus further including a second set cover members and second bottom seal means each arranged in a transverse row parallel to said first set of cover members and said first bottom seal means, said second set of cover members and said second bottom seal means being arranged so that when said sampling containers of said first transverse row are at said sampling station in alignment with said first set of cover members and said first bottom seal means, said sampling containers of said second transverse row are in alignment with said second set of cover members and said second bottom seal means.

17. The sampling apparatus of claim 16 further including pump means for each of said sampling containers, each of said pump means being associated with at least one of said first and second fluid conducting means associated with each of said sampling containers for pumping fluid into and out of said chambers of said sampling containers.

18. The sampling apparatus of claim 17 wherein said pump means associated with said first transverse row of sampling containers are driven by a first common drive device.

19. The sampling apparatus of claim 18 further including a second common drive device for driving said pump means associated with said second transverse row of sampling containers.

20. Sampling apparatus for obtaining a plurality of fluid samples, comprising:
a plurality of sampling containers each having a chamber therein for receipt of a fluid, each of said sampling containers including individual agitating means associated with said chamber thereof and operable for agitating material in said chamber, each of said individual agitating means comprising a rotatable agitating member mounted in said chamber of its associated sampling container and an agitator drive shaft connected to said agitating member and extending out of the bottom of its associated sampling container, each of said sampling containers including operating means for operating each of said individual agitating means of said sampling containers when said sampling containers are positioned at said sampling station, said operating means comprising rotating means for rotating said agitator drive shafts, said rotating means comprising a rotatable drive member mounted on said bottom support means for each of said agitator drive shafts and means for rotating each of said rotatable drive members, each of said associated agitator drive shafts and rotatable drive members including drive coupling means for coupling said rotatable drive members and associated agitator drive shafts so that each of said agitator drive shafts is rotated when said associated rotatable drive members are rotated;

drive means for simultaneously moving said plurality of sampling containers to a sampling station;

first fluid conducting means for each of said sampling containers for conducting fluid into each of said sampling containers when said sampling containers are positioned at said sampling station;

second fluid conducting means for each of said sampling containers for withdrawing a fluid sample from each of said sampling containers when said sampling containers are positioned at said sampling station;

coupling means located at said sampling station for coupling said first and second fluid conducting means with said chambers of each of said sampling containers when said sampling containers are positioned at said sampling station, said coupling means including sealing means for individually sealing said chamber for each of said sampling containers when said first and second fluid conducting means are coupled to said sampling containers; and bottom support means for supporting the bottom of said sampling containers at said sampling station, said drive means being operable to lower said plurality of sampling containers onto said bottom support means and each of said rotatable drive members having an opening therein for receipt of an associated one of said agitator drive shafts when said sampling containers are lowered onto said bottom support means.

21. The sampling apparatus of claim 20 wherein said opening in each of said rotatable drive members is of a larger lateral dimension than the lateral dimension of its associated agitator drive shaft so as to ensure receipt of said associated agitator drive shaft into said opening of said associated rotatable drive member when said sampling containers are lowered onto said bottom support means.

22. Sampling apparatus for obtaining a plurality of fluid samples, comprising:

a plurality of sampling containers each having a chamber therein for receipt of a fluid, each of said sampling containers including an inlet opening for introducing a fluid into said chamber and an outlet opening for withdrawing a fluid sample from said chamber, said inlet and outlet openings being arranged to communicate with said chamber at first and second portions respectively of said chamber, each of said sampling containers including individual agitating means associated with said chamber thereof and operable for agitating material in said chamber, each of said individual agitating means comprising a rotatable agitating member mounted in said chamber of its associated sampling container and an agitator drive shaft connected to said agitating member and extending out of the bottom of its associated sampling container, said rotatable agitating member of each of said sampling containers being positioned intermediate of said first and second portions of said chamber of each said sampling containers, each of said sampling containers including operating means for operating each of said individual agitating means of said sampling containers when said sampling containers are positioned at said sampling station, said operating means comprising rotating means for rotating said agitator drive shafts;

drive means for simultaneously moving said plurality of sampling containers to a sampling station;

first fluid conducting means for each of said sampling containers for conducting fluid into each of said sampling containers when said sampling containers are positioned at said sampling station; and second fluid conducting means for each of said sampling containers for withdrawing a fluid sample from each of said sampling containers when said sampling containers are positioned at said sampling station;

coupling means located at said sampling station for coupling said first and second fluid conducting means with said chambers of each of said sampling containers when said sampling containers are positioned at said sampling station, said coupling means including sealing means for individually sealing said chamber for each of said sampling containers when said first and second fluid conducting means are coupled to said sampling containers.

23. Sampling apparatus for obtaining a plurality of fluid samples, comprising:

a plurality of sampling containers each having a chamber therein for receipt of a fluid, each of said sampling containers including individual agitating means associated with said chamber thereof and operable for agitating material in said chamber thereof, each of said individual agitating means comprising a rotatable agitating member mounted in said chamber of its associated sampling container and an agitator drive shaft connected to said agitating member and extending out of the bottom of its associated sampling container;

drive means for simultaneously moving said plurality of sampling containers to a sampling station;

first fluid conducting means for each of said sampling containers for conducting fluid into each of said sampling containers when said sampling containers are positioned at a first sampling station;

second fluid conducting means for each of said sampling containers for conducting a fluid sample from each of said sampling containers when said sampling containers are positioned at said sampling station;

operating means for operating each of said individual agitating means for said sampling containers when said sampling containers are positioned at said sampling station, said operating means comprising rotating means for rotating said agitator drive shafts; and bottom support means for supporting the bottom of said sampling containers at said sampling station; wherein said drive means is operable to lower said plurality of sampling containers onto said bottom support means; wherein said rotating means comprises a rotatable drive member mounted on said bottom support means for each said agitator drive shafts, each of said rotatable drive members having an opening therein for receipt of an associated one of said agitator drive shaft when said sampling containers are lowered into said bottom support means, each of said associated agitator drive shafts and rotatable drive members including drive coupling means for coupling said rotatable drive members and associated agitator drive shafts so that each of said agitator drive shafts is rotated when said associated rotatable drive members are rotated; and wherein said rotating means further includes means for rotating each of said rotatable drive members.

24. The sampling apparatus of claim 23 wherein said opening in each of said rotatable drive members is of a larger lateral dimension than the lateral dimension of its associated agitator drive shaft so as to ensure receipt of said associated agitator drive shaft into said opening of said associated rotatable drive member.

25. Sampling apparatus for obtaining a plurality of fluid samples, comprising:

a plurality of sampling containers each having a chamber therein for receipt of a fluid, each of said sampling containers including an inlet opening for introducing a fluid into said chamber and an outlet opening for withdrawing a fluid sample from said chamber, said inlet and outlet openings being arranged to communicate with said chamber at first and second portions respectively of said chamber, each of said sampling containers including individual agitating means associated with said chamber thereof and operable for agitating material in said chamber thereof, each of said individual agitating means comprising a rotatable agitating member mounted in said chamber of its associated sampling container and an agitator drive shaft connected to said agitating member and extending out of the bottom of its associated sampling container, said rotatable agitating member being positioned intermediate of said first and second portions of said chamber of each said sample containers;

drive means for simultaneously moving said plurality of sampling containers to a sampling station;

first fluid conducting means for each of said sampling containers for conducting fluid into each of said sampling containers when said sampling containers are positioned at a first sampling station;

second fluid conducting means for each of said sampling containers for conducting a fluid sample from each of said sampling containers when said sampling containers are positioned at said sampling station; and operating means for operating each of said individual agitating means for said sampling containers when said sampling containers are positioned at said sampling station, said operating means comprising rotating means for rotating said agitator drive shafts.

* * * * *